(12) United States Patent
Guo et al.

(10) Patent No.: US 10,918,773 B2
(45) Date of Patent: Feb. 16, 2021

(54) COLLAPSIBLE AND SELF-EXPANDING CANNULA FOR A PERCUTANEOUS HEART PUMP AND METHOD OF MANUFACTURING

(71) Applicant: TCI LLC, St. Paul, MN (US)

(72) Inventors: Xiaoping Guo, Eden Prairie, MN (US); David Panus, Maple Grove, MN (US)

(73) Assignee: TCI LLC, St. Paul, MN (US)

( * ) Notice: Subject to any disclaimer, the term of this patent is extended or adjusted under 35 U.S.C. 154(b) by 47 days.

(21) Appl. No.: 16/296,592

(22) Filed: Mar. 8, 2019

(65) Prior Publication Data

US 2019/0290817 A1 Sep. 26, 2019

Related U.S. Application Data

(60) Provisional application No. 62/647,883, filed on Mar. 26, 2018.

(51) Int. Cl.
*A61M 1/10* (2006.01)
*A61M 1/12* (2006.01)

(52) U.S. Cl.
CPC ........ *A61M 1/1072* (2013.01); *A61M 1/1024* (2014.02); *A61M 1/122* (2014.02); *A61M 1/125* (2014.02); *A61M 1/1008* (2014.02); *A61M 1/1034* (2014.02)

(58) Field of Classification Search
CPC .. A61M 1/1072; A61M 1/1024; A61M 1/122; A61M 1/125; A61M 1/1034; A61M 1/1008

USPC .......................................................... 600/16
See application file for complete search history.

(56) References Cited

U.S. PATENT DOCUMENTS

| | | | |
|---|---|---|---|
| 6,790,171 B1 * | 9/2004 | Grundeman | A61M 25/0023 600/18 |
| 8,597,170 B2 | 12/2013 | Walters et al. | |
| 8,721,517 B2 | 5/2014 | Zeng et al. | |
| 9,327,067 B2 | 5/2016 | Zeng et al. | |
| 9,358,329 B2 | 6/2016 | Fitzgerald et al. | |
| 2011/0106115 A1 * | 5/2011 | Haselby | A61B 5/14535 606/151 |

(Continued)

OTHER PUBLICATIONS

Fuentes et al. "Phase Change Behavior of Nitinol Shape Memory Alloys," Advanced Engineering Materials, 2002, 4, No. 7, 437-451.

(Continued)

*Primary Examiner* — Amanda K Hulbert
*Assistant Examiner* — Philip C Edwards
(74) *Attorney, Agent, or Firm* — Armstrong Teasdale LLP

(57) ABSTRACT

Disclosed herein is a collapsible and self-expanding cannula for a percutaneous heart pump. The collapsible and self-expanding cannula comprises an open proximal end, an open distal end, and an elongate fluid-impermeable wall structure that includes a first balloon film, a cannula strut, and a second balloon film. The first balloon film is disposed on an interior surface of the cannula, the second balloon film is disposed on the exterior surface of the cannula, and the cannula strut is between the two balloon films. Together they form an integrated hybrid structure upon thermal fusion bonding. Also disclosed herein is a method of manufacturing the collapsible and self-expanding cannula.

17 Claims, 10 Drawing Sheets

(56) References Cited

U.S. PATENT DOCUMENTS

2012/0004496 A1* 1/2012 Farnan .................. A61M 1/101
                                                                              600/16

OTHER PUBLICATIONS

Spini et al. "Transition temperature range of thermally activated nickel-titanium archwires", J. Appl. Oral Sci. 2014:22 (2)109-117.

* cited by examiner

COLLAPSIBLE AND SELF-EXPANDING CANNULA FOR A PERCUTANEOUS HEART PUMP AND METHOD OF MANUFACTURING

CROSS REFERENCE TO RELATED APPLICATIONS

This application claims priority to provisional application Ser. No. 62/647,883, filed Mar. 26, 2018, which is incorporated herein in its entirety.

BACKGROUND OF THE DISCLOSURE a. Field of the Disclosure

The present disclosure relates generally to percutaneous heart pumps including a collapsible and self-expanding cannula fabricated from a shape memory alloy, such as nitinol. More specifically, the present disclosure relates to a collapsible and self-expanding cannula that includes an open proximal end, an open distal end, and an elongate fluid-impermissible wall structure formed from an inner balloon layer, a cannula strut and an outer balloon layer that are thermally fused into an integrated hybrid cannula structure, and methods of manufacturing the same.

b. Background Art

Heart disease is a major health problem that claims many lives per year. After a heart attack or other major cardiac event, only a small number of patients can be treated with medicines or other non-invasive treatment. A significant number of patients, however, can recover from a heart attack or other cardiac event if provided with mechanical circulatory support in timely manner.

In one conventional approach for treating patients, a blood pump having a fixed cross-section is surgically inserted into a heart chamber, such as into the left ventricle of the heart and the aortic arch, to assist the pumping function of the heart. Other known conventional applications involve providing for pumping venous blood from the right ventricle to the pulmonary artery for support of the right side of the heart. The object of the surgically inserted pump is to reduce the load on the heart muscle for a period of time allowing the affected heart muscle to recover and heal. In some cases, surgical insertion may potentially cause additional stresses in heart failure patients.

In many cases, percutaneous insertion of a left ventricular assist device ("LVAD"), a right ventricular assist device ("RVAD"), or in some cases a system for both sides of the heart (sometimes called biVAD) is a desirable alternative. To allow for percutaneous insertion, the pump component of the device is collapsible with self-expandability and includes an impeller encased in a cannula, while blood, driven by the impeller, traverses the interior of the cannula.

During insertion and use of the percutaneous heart pump, it is desirable that the lubricity and integrity of the surfaces of the pump that are exposed to the patient vasculature be maximized. This maximization of the lubricity and integrity reduces the potential for blood hemolysis and irritation at the intravascular location of the pump. Improving the lubricity of the surfaces in such devices that interact with the vasculature of a patient (e.g., the blood or the blood vessels) will improve their effectiveness and further improve patient outcomes.

SUMMARY OF THE DISCLOSURE

In one embodiment the present disclosure relates to a collapsible and self-expanding cannula for a percutaneous heart pump. The collapsible and self-expanding cannula comprises: (i) an open proximal end; (ii) an open distal end; and (iii) an elongate, fluid impermissible wall structure. The elongate, fluid impermissible wall structure comprises: (a) a first balloon film disposed on an interior surface of the wall structure and defining a first wall structure circumferential surface; (b) a second balloon film disposed on an exterior surface of the wall structure and defining a second wall structure circumferential surface; and (c) a cannula strut disposed between the first balloon film and the second balloon film.

In another embodiment the present disclosure is directed to a method of manufacturing a collapsible and self-expanding cannula for a percutaneous heart pump. The method comprises: introducing a first balloon film onto a supporting mandrel; expanding a cannula strut; introducing the expanded cannula strut onto the supporting mandrel such that the expanded cannula strut contacts and fits against the first balloon film; introducing a second balloon film onto the supporting mandrel such that the second balloon film contacts and fits against the expanded cannula strut; introducing a shrink tube onto the supporting mandrel such that the shrink tube contacts and fits against the second balloon film and wraps around a surface of the second balloon film thereby creating a balloon-strut-balloon assembly; heating the balloon-strut-balloon assembly so that at least one of the first balloon film and the second balloon film at least partially melts and at least partially adheres to the expanded cannula strut such that spaces within the balloon-strut-balloon assembly are filled up by polymer melt under an inward radial pressure exerted by the shrink tube thereby creating a fused balloon film; and removing the shrink tube.

DETAILED DESCRIPTION OF THE DISCLOSURE

Figure 1:
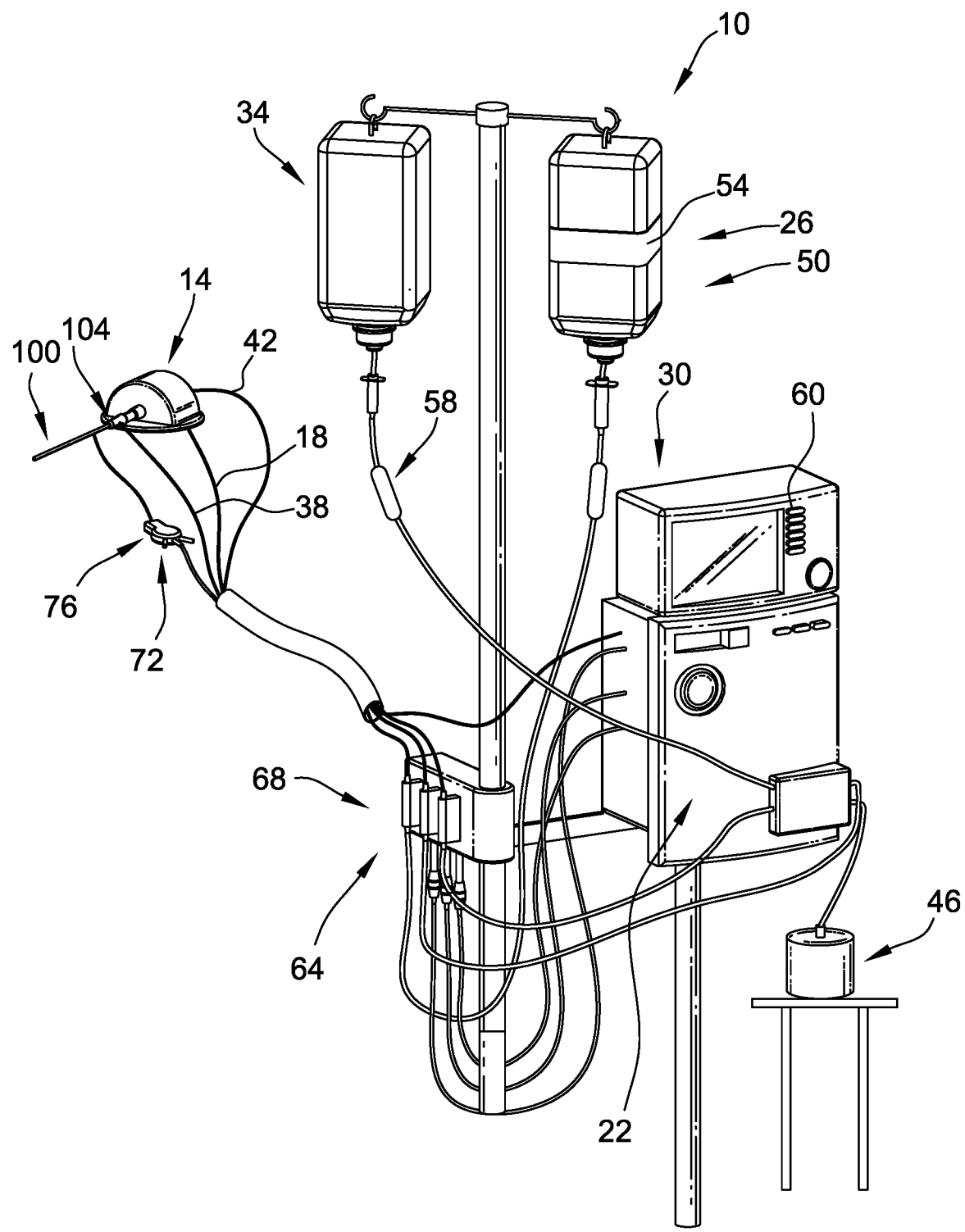
FIG. 1 illustrates one embodiment of a heart pump configured for percutaneous application and operation.

Percutaneous heart pumps are generally designed to provide circulatory support for a patient suffering from a cardiac deficiency. Support can be short term or long term, depending on the nature of the deficiency. A typical percutaneous heart pump includes at least an inner sheath, an outer sheath, an impeller-type pump disposed distally on the inner sheath, an external motor, a control console and other accessories. When the device is deployed in the human anatomy, the inner sheath is relatively stationary, while the outer sheath, with respect to the inner sheath, is axially moveable. The pump unit is disposed along the distal portion of the inner sheath and comprises an impeller and a cannula. The cannula is foldable and/or collapsible based on forces exerted upon it by the outer sheath; as such, the cannula is generally self-expanding. The collapsed profile, also commonly referred to as the low insertion (or stored) profile, is where the cannula is radially compressed due to the compressive force exerted upon it by the outer sheath. When the outer sheath is slidably removed, the self-expanding cannula expands to its operating (or pumping) profile. This expansion is due to the superelastic polymers and shape memory alloys that are used to fabricate the cannula. Although a number of embodiments of the present disclosure are described herein including a self-expanding cannula, one skilled in the art will appreciate that other embodiments, such as where the cannula is not self-expanding, are also within the scope of the present disclosure.

It is generally desirable for the outer sheath as described herein to easily slide off of the self-expanding cannula in order for the percutaneous heart pump to operate effectively and efficiently. If the surfaces between the cannula and the outer sheath stick together or catch, it may potentially reduce the overall integrity of one or both surfaces. The process is reversed when the pump is removed from the patient. The outer sheath slides over and collapses the cannula thereby reducing its profile and easing removal. The present disclosure provides an improved collapsible and self-expanding cannula for use in combination with a percutaneous heart pump that is fabricated in a manner that provides excellent lubricity of the collapsible and self-expanding cannula's surfaces and reduces the likelihood of damage or degradation during unsheathing and resheathing operations.

The improved collapsible and self-expanding cannula as disclosed herein exhibits improved lubricity and overall performance through the use of specific materials from which the collapsible and self-expanding cannula is fabricated and by the manner in which fabrication is done. The collapsible and self-expanding cannula of the present disclosure generally is a hybrid composite structure comprising three components: a first (inner) balloon film, a cannula strut (also called a stent) formed from a shape memory alloy, and a second (outer) balloon film. The first and second balloon films may independently comprise one or a plurality of polymer-based layers. Once suitably positioned, these three components (i.e., the first and second balloon films and the cannula strut) are at least partially thermally fused and integrated together to create an integrated cannula with a wall structure that has a substantially smooth, continuous inner or interior surface and a substantially smooth, continuous outer or exterior surface to facilitate use in the percutaneous heart pump. Substantially smooth generally means that the surface does not impede or otherwise obstruct the flow of blood through the lumen of the collapsible and self-expanding cannula or resist the advancement or retraction of the heart pump in the catheter assembly. By way of illustration and not limitation, a substantially smooth surface would feel generally smooth to the touch.

As used herein, the collapsible and self-expandable cannula is alternatively referred to as the "self-expanding cannula" or, simply, the "cannula". In all aspects herein, these terms are used interchangeably and refer to the same structure. In contrast, the "cannula strut" refers to one of the components used to make the self-expandable and collapsible cannula, and, in many embodiments, comprises the shape memory alloy (e.g., nitinol) which imparts the superelasticity and shape memory that permits the cannula to collapse and return to its expanded configuration.

a. Heart Pump System Overview

Figure 2:
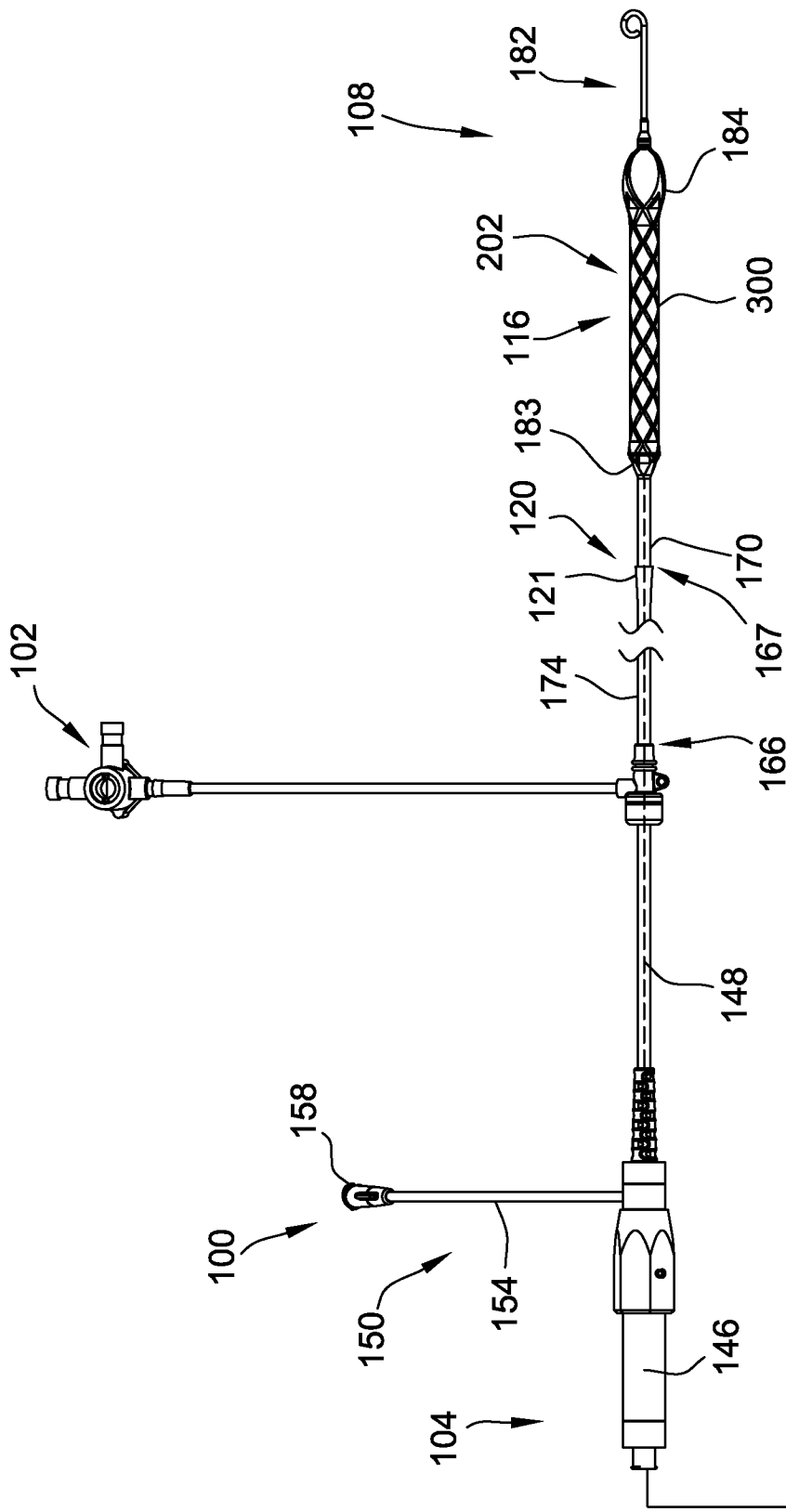
FIG. 2 is a plan view of one embodiment of a catheter delivery assembly adapted to be used with a percutaneous heart pump.

Referring now to the Figures, and specifically to FIG. 1, there is illustrated one embodiment of a heart pump 10 that includes a catheter assembly 100 having a proximal end 104 adapted to connect to a motor 14 and a distal end 108 (as shown in FIG. 2) adapted to be inserted percutaneously into a patient (not shown in FIG. 1). Motor 14 is connected by a signal line 18 to a control module 22 that provides power and/or control signals to motor 14. Heart pump 10 may have an infusion system 26 and a patient monitoring system 30.

Infusion system 26 can provide a number of benefits to heart pump 10. In one embodiment, infusion system 26 includes a source of infusant 34, a fluid conduit 38 extending from infusant source 34 to proximal end 104 of catheter assembly 100 and a fluid conduit 42 extending from proximal end 104 of catheter assembly 100 to a waste container 46. The flow of an infusant to and from catheter assembly 100 can be by any means, including a gravity system or one or more pumps. In FIG. 1, infusant source 34 includes an elevated container 50, which may be saline or another infusant as necessary based on patient requirements. Flow from elevated container 50 can be regulated by a pressure cuff 54 to elevate the pressure of the fluid in container 50 to increase flow or by a pinch valve 58 or by other means.

With continuing reference to FIG. 1, patient monitoring system 30 can be used to monitor the operation of the patient and/or pump 10. For example, patient monitoring system 30 can include a user interface 60 coupled with a source of data 64. Data source 64 can include one or more patient condition sensors, such as pressure sensors 68 that are in pressure communication with the patient and/or operating components within the patient. In one embodiment, pressure sensors 68 fluidly communicate by a conduit 72 that extends between the sensors and a proximal portion of catheter assembly 100. Conduit 72 can include a plurality of separable segments and can include a valve 76 to enable or disable the pressure communication to sensors 68.

Heart pump 10 is adapted to provide an acute or other short-term treatment. A short-term treatment can be for less than a day or up to several days or weeks in some cases. With certain configurations heart pump 10 can be used for a month or more.

FIG. 2 illustrates one embodiment of catheter assembly 100 to be used with heart pump 10 (see FIG. 1). An impeller assembly 116 disposed at distal end 108 of catheter assembly 100 is configured to pump blood proximally or distally through or along a portion of heart pump 10 (see FIG. 1) to convey blood from one body cavity to another. Impeller assembly 116 can be arranged to pump blood distally, such as in a right heart assist mode to move blood from the right ventricle to the pulmonary artery. Proximal flow is optimal for left heart support to move blood from the left ventricle to the aorta. Heart pump 10 (see FIG. 1) can be used to treat patients with acute heart failure, ST elevation myocardial infarction (STEMI), cardiac arrest, cardiac arrhythmia or other heart maladies as noted above. Heart pump 10 (see FIG. 1) also can be used in connection with a surgical treatment to support the patient without providing full cardiovascular bypass. A patient could be supported on the device for longer term with proper controls and design.

One feature that facilitates percutaneous insertion is providing catheter assembly 100 with a low profile configuration. For example, distal end 108 of catheter assembly 100 can be configured to have about an 11 French (approximately 3.5 mm) size in a first configuration for insertion and an expanded configuration, such as up to about 21 French (approximately 7 mm) once in place in the body. The larger size facilitates greater flow rates by impeller assembly 116. Of course, other sizes for insertion and expansion configurations are within the scope of the present disclosure.

Catheter assembly 100 is configured to enable distal end 108 to reach a heart chamber after being inserted initially into a peripheral vessel. For example, catheter assembly 100 can have a suitable length to reach the left ventricle and sufficient pushability and torquability to traverse the intervening vasculature. Catheter assembly 100 may include a multilumen catheter body 120 that is arranged to facilitate delivery and operation of an impeller (see FIG. 3) of impeller assembly 116. Multilumen catheter body 120 includes outer sheath assembly 121 and inner sheath assembly 170. Further details concerning various embodiments of multilumen catheter body 120 are described in more detail in U.S. Pat. No. 8,597,170.

A drive system is provided to drive an impeller within impeller assembly 116. The drive system includes motor 14 and a drive controller, which can be integrated into control module 22 (see FIG. 1). Although motor 14 may be configured to be disposed outside the patient, some structures and assemblies described herein could be incorporated into a system in which a motor is miniaturized sufficiently to be inserted into the patient in use, including into the vasculature.

A torque coupling system is provided for transferring torque from motor 14 to impeller assembly 116. The torque coupling system is discussed further in U.S. Pat. No. 8,597,170, but in general can include a mechanical or magnetic interface disposed between the motor 14 and drive assembly 146 that is disposed at proximal end 104 of catheter assembly 100. The drive assembly 146 is coupled with the proximal end of inner sheath assembly 170 and provides an elongate drive cable 148 extending from the drive assembly 146, via center lumen of inner sheath assembly 170, to the impeller shaft (see FIG. 3) of impeller assembly 116 where the drive cable 148 is securely affixed onto, or coupled with, an impeller shaft (see FIG. 3) or an impeller assembly 116. Thus, motor 14 is coupled with a drive assembly 146 and directly drives the impeller to spin inside a cannula assembly 202 (which comprises a self-expanding cannula 300 and a flexible atraumatic tip 182) with self-expanding cannula 300 being affixed to the distal end of multilumen catheter body 120 at inner sheath assembly 170. In the embodiment shown in FIG. 2, self-expanding cannula 300 comprises an open proximal end 183 and an open distal end 184. Further, as described in detail below, in some embodiments, self-expanding cannula 300 includes an elongate fluid-impermissible (i.e., impermeable) wall structure 159 (see FIG. 3) where an impeller 165 coupled with the drive cable 148 is disposed. Other embodiments, where elongate wall structure 159 is not completely fluid-impermissible are also within the scope of the present disclosure.

FIG. 2 also shows an infusion inflow assembly 150 that can form a part of infusion system 26 (see FIG. 1). The infusion in flow assembly 150 is provided adjacent proximal end 104 in one embodiment. Infusion system 26 (see FIG. 1) is configured to convey one or more fluids therein in connection with operation of impeller assembly 116 or the conducting of the treatment. In one embodiment, an infusant, e.g., a medication or a lubricating fluid, such as saline or other beneficial medium, is conveyed distally along the pump, e.g., within multilumen catheter body 120, toward the operating components adjacent to distal end 108. The infusant can include lubrication fluids such as glucose or other biocompatible lubricants. Infusion inflow assembly 150 includes an extension tube 154 having a luer or other suitable connector 158 disposed at a proximal end thereof and an inflow port in fluid communication with one or more lumens within catheter assembly 100. A lumen extending through extension tube 154 is adapted to be fluidly coupled with a fluid source connected to connector 158, to deliver the fluid into catheter assembly 100 through one or more flow paths.

Figure 3:
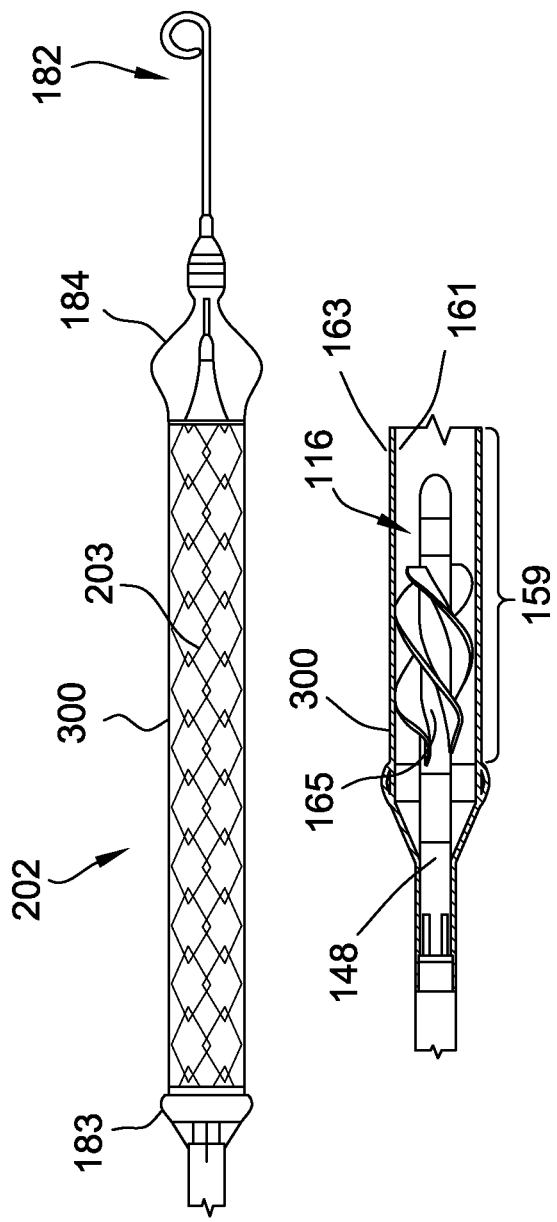
FIG. 3 is one embodiment of an impeller assembly in a percutaneous heart pump.

FIG. 3 illustrates one embodiment of cannula assembly 202 that may be disposed and affixed near the distal end of inner sheath assembly 170 (shown in FIG. 2). Self-expanding cannula 300 of cannula assembly 202 houses impeller 165. Self-expanding cannula 300 comprises a fluid-impermissible elongate wall structure 159 having an interior surface 161 and an exterior surface 163. In some aspects, the clearance between interior surface 161 of self-expanding cannula 300 and an impeller 165 is minimal to prevent harmful interactions therebetween during operation. Impeller 165 is carefully placed within self-expanding cannula 300 and journaled to inner sheath assembly 170 such that impeller 165, as driven by drive cable 148, freely rotates within self-expanding cannula 300 to maintain an appropriate pumping flow regime, e.g., from the distal side to the proximal side of self-expanding cannula 300. FIG. 3 shows that, in some embodiments, self-expanding cannula 300 includes a cannula strut 203 that forms a cage or mesh structure of filaments that extend axially along self-expanding cannula 300 and wraps circumferentially around a central area of self-expanding cannula 300 in which impeller 165 of impeller assembly 116 is disposed. Cannula strut 203 can take any suitable form, such as being constructed to provide radial collapsibility and self-expandability. Self-expanding cannula 300 forms its impermissible elongate wall structure 159 by encapsulating the middle portion of cannula strut 203 with polymer layers so that the rotating impeller transfers the blood flow from the distal side to the proximal side of self-expanding cannula 300 during use of the heart pump system. In some embodiments, cannula strut 203 is a metallic mesh comprising a shape memory alloy.

Catheter assembly 100 includes outer sheath assembly 121 (shown in FIG. 2) configured to constrain impeller assembly 116 in a low profile configuration in a first state and to permit impeller assembly 116 to expand to an enlarged configuration in a second state. Outer sheath assembly 121 has a proximal end 166, a distal end 167, and an elongate sheath body 174 extending therebetween (all shown in FIG. 2). Outer sheath assembly 121 provides a passageway for inner sheath assembly 170 to be sleekly disposed through outer sheath assembly 121. This arrangement permits inner sheath assembly 170 to be positioned between an advanced position corresponding to the low profile configuration of the heart pump and a retracted position corresponding to the enlarged configuration of the heart pump. In some embodiments, a luer 102 or other suitable connector is in fluid communication with proximal end 166, distal end 167, and elongate sheath body 174 extending therebetween of outer sheath assembly 121. Luer 102 can be configured to deliver fluids to catheter assembly 100, such as priming fluid, infusant, or any other suitable fluid.

FIGS. 2 and 3 also show an atraumatic tip 182 disposed distal to self-expanding cannula 300. Atraumatic tip 182 can have an arcuate configuration such that interactions with a patient's internal tissues are controlled and do not cause trauma thereto. Atraumatic tip 182 can take any suitable shape, which can vary depending on the degree of curvature of the tip. The tip is designed to be atraumatic so that after retraction of the guidewire, when the tip is left inside, for example, a ventricle, it does not cause injury or trauma to the inner wall or endocardial surface of the ventricle resulting from motion of the ventricle.

Atraumatic tip 182 can include a 180° bend, wherein the distal-most end of atraumatic tip 182 is generally parallel to the non-arcuate portion of atraumatic tip 182, but extending in the opposite direction (e.g., a j-tip). The distal-most end of atraumatic tip 182 can be generally perpendicular to the non-arcuate portion of atraumatic tip 182, or at an angle between about 90° and about 180°. In yet another aspect, the distal-most end of atraumatic tip 182 can include a 360° bend, wherein the distal-most end of atraumatic tip 182 is generally parallel to the non-arcuate portion of atraumatic tip 182, while extending in generally the same direction. In some embodiments, the arcuate portion of atraumatic tip 182 can be coiled greater than 360°.

b. Collapsible and Self-Expanding Cannula

The collapsible and self-expanding cannula of the present disclosure as described herein includes open proximal end 183, open distal end 184, and an elongate fluid-impermissible wall structure, such as wall structure 159 shown FIG. 3. Elongate fluid-impermissible wall structure 159 is formed from a first balloon film having interior surface 161, cannula strut 203, and a second balloon film having exterior surface 163 that are thermally fused together into an integrated hybrid cannula structure.

Cannula strut 203 is generally formed from a shape memory alloy. In this embodiment, cannula strut 203 includes an elongate portion that extends from open proximal end 183 to open distal end 184. In one embodiment, the first balloon film disposed on an inside surface of cannula strut 203 and the second balloon film is disposed on an outer surface of cannula strut 203. Collapsible and self-expanding cannula 300 is formed in such a manner (as described in detail below) so that that the first balloon film and the second balloon film are seamlessly integrated together to encapsulate cannula strut 203 and form fluid-impermissible wall structure 159 having interior surface 161 and exterior surface 163. The first and second balloon films comprise polymeric materials and are shaped via blow molding as disclosed elsewhere herein. Elongated, fluid-impermissible wall structure 159 of cannula 300 enables the pumping functionality of a percutaneous heart pump where impeller 165 of impeller assembly 116 transfers the blood from open distal end 184 to open proximal end 183 of cannula 300. The polymeric wall structure of such cannula 300 has excellent surface lubricity attributes that allow for smooth advancement and retraction of a sheath assembly and minimizes abrasive damage on rotating impeller blades in impeller assembly 116 for the heart pump.

Figure 4:
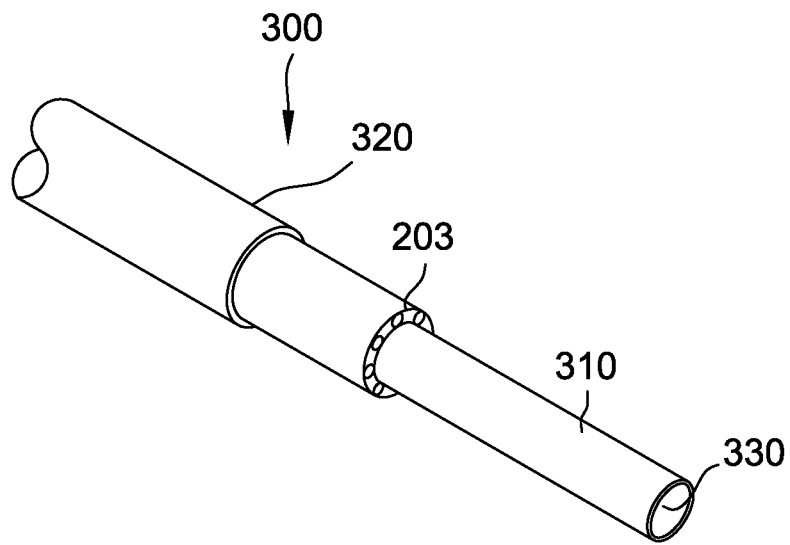
FIG. 4 illustrates one embodiment of a collapsible and self-expandable cannula including a first balloon film, a cannula strut and a second balloon film.

Referring now to FIG. 4, there is illustrated a cut away diagram of self-expanding cannula 300 in accordance with one embodiment of the present disclosure. Self-expanding cannula 300 comprises elongate, fluid-impermissible wall structure 159 (shown in FIG. 2) formed by thermally integrating a first (inner) polymer balloon film 310, metallic cannula strut 203, and a second (outer) polymer balloon film 320 together. First balloon film 310 is disposed on the interior surface of metallic cannula strut 203 to form interior surface 161 (shown in FIG. 3) of self-expanding cannula 300, and second balloon film 320 is disposed on the exterior surface of metallic cannula strut 203 to form exterior surface 163 (shown in FIG. 3) of self-expanding cannula 300. Metallic cannula strut 203 is disposed between first balloon film 310 and second balloon film 320; that is, first balloon film 310 is disposed about an interior circumference of cannula strut 203 and second balloon film 320 is disposed about an exterior circumference of cannula strut 203. Impeller 165 (shown in FIG. 3) may be disposed within a lumen 330 of self-expanding cannula 300 to pump blood from open distal end 184 to open proximal end 183 during operation of a percutaneous heart pump when impeller 165 rotates at a high speed. For example, when a heart pump comprising self-expanding cannula 300 is collapsed to its low insertion profile and advanced from the femoral artery into the left ventricle through the aortic arch of the heart, self-expanding cannula 300 is deployed across the aortic valve and then fully expanded into the operating configuration upon the retraction of a sheath assembly. When impeller 165 spins at a high speed, the oxygen-rich blood is pulled from open distal end 184 of cannula 300 within the left ventricle, pumped through elongate fluid-impermissible wall structure 159 of cannula 300, and sent to the ascending aorta and the body through open proximal end 183 of cannula 300. Once a period of support is completed, outer sheath assembly 121 (shown in FIG. 1) is advanced to re-collapse the heart pump such that cannula 300 and impeller assembly 116 are in a low profile configuration and can be removed from the body.

Figure 5:
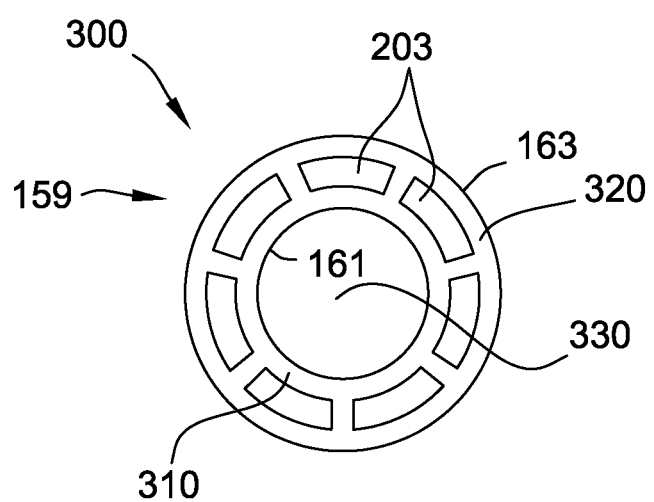
FIG. 5 is a cross-sectional view of the collapsible and self-expandable cannula of FIG. 4.

Referring now to FIG. 5, there is illustrated a cross-sectional view of elongate, fluid-impermissible wall structure 159 of self-expanding cannula 300 of FIG. 4. As shown in FIGS. 4 and 5, interior surface 161 of self-expanding cannula 300 is formed of first polymer balloon film 310, and it is exposed to and may be in contact with the blades of an impeller (not shown) comprising impeller assembly. Exterior surface 163 of self-expanding cannula 300 is formed of second polymer balloon film 320, and is exposed to, and may be in contact with, both blood vessels (not shown) and heart tissue (not shown). Both interior surface 161 and exterior surface 163 of elongate wall structure 159 of self-expanding cannula 300 (i.e., both first balloon film 310 and second balloon film 320) are exposed to, and directly in contact with, the blood.

In many embodiments of the present disclosure, cannula strut 203 of self-expanding cannula 300 is formed from a shape memory alloy. Cannula strut 203 is generally in the form of a braided mesh, a weaved mesh, or is laser-cut into an interconnected, maze-like pattern that allows for collapsing and self-expanding. To make impeller assembly 116 function as a screw-type, positive displacement pump, elongate structure 159 of cannula 300 where impeller 165 is disposed has to be fluid impermissible. Because cannula strut 203 in the form of braided memory shape mesh or laser-cut pattern or woven mesh is not fluid tight due to its required attributes of collapsibility or self-expanding, as illustrated in FIG. 5, the elongate portion of cannula strut 203 is encapsulated by first (or inner) polymer balloon film 310 and second (or outer) polymer balloon film 320, and thermally fused into a hybrid structure comprising fluid-impermissible, thin wall structure 159 having interior surface 161 and exterior surface 163 as described herein. Such a hybrid structure of cannula 300 still exhibits comparable collapsibility and self-expandability as an unencapsulated cannula strut (i.e., cannula strut 203 without first balloon film 310 and second balloon film 320). As described more fully below, first balloon film 310 and second balloon film 320 desirably substantially adhere and/or fuse together wherein they may be physically in contact each other, or both balloon films preferably adhere to cannula strut 203 wherein first balloon film 310 and second balloon film 320 may be physically in direct contact with cannula strut 203, and thus provide a fluid-impermissible, seamless self-expanding cannula 300 that resists delamination.

Shape memory alloys (SMA) suitable for use in construction of cannula strut 203 are metallic alloy materials that have the ability to "memorize" or retain its previous shape when subjected to certain stimuli, such as stress or heat. An SMA material, like nitinol, may also possess superelasticity that allows a component comprising such a material to exhibit pseudo-elastic recovery or "memory" from one shape to another multiple times upon the application and release of deforming stress or force. A small stress or force may induce considerable deformation, but the material or component comprising such a material recovers its original shape when the deforming force or stress is released. There is no need for any other stimulus, such as heating or cooling, for the deformed material to return to its original shape. The superelasticity of such an SMA material is a mechanical type of shape memory that is utilized for making cannula strut 203 exhibiting the reversible collapsing and self-expanding capacity. Under applied force or stress, the cannula material is deformed to a lower insertion configuration. Because it is fabricated from an SMA, it "memorizes" its original shape and returns thereto upon the release of the deforming force or stress.

Figure 10:
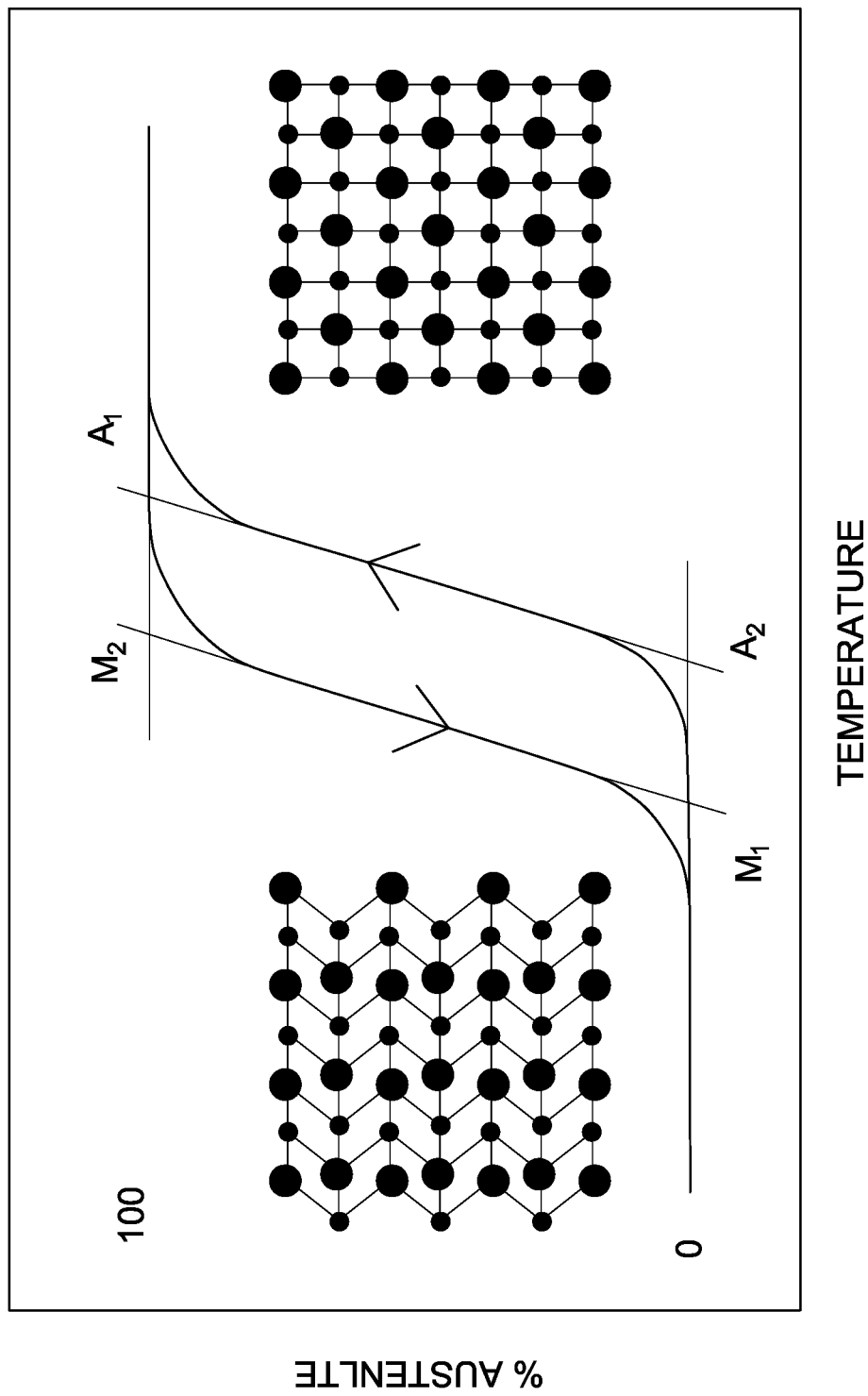
FIG. 10 is a graph illustrating the austenite-martensite transition of a typical shape memory alloy.

SMAs generally display two distinct crystal forms: martensite primarily with variant sheared platelets, and austenite (the parent or memory phase) with long-range order. The martensite of an SMA material is self-accommodating and deforms by a so-called twining mechanism that transforms different sheared platelet variants to the variant accommodating to the maximum deformation in the direction of the applied force. At low temperatures, an SMA material may exist as martensite that can be deformed by a relatively small force. In contrast, at high temperatures, the material may exist as austenite which is hard to deform like normal metals. Therefore, upon thermal stimulus (heating or cooling), an SMA material may undergo phase transformation as temperature increases or decreases. For example, when heated, an SMA material that exists as martensite (e.g., ambient or body temperature) may start to undergo the phase transformation-to-austenite at a so-called "Austenite-Start temperature" ($A_s$ or $A_2$) and finish the transformation at a relatively high, so-called "Austenite-Finish temperature" ($A_f$ or $A_1$), above which the material exists as austenite (i.e., the parent or memory phase), displaying shape memory. Similarly, upon cooling, an SMA material that exists as austenite may start to undertake the transformation-to-martensite at a so-called "Martensite-Start temperature" ($M_s$ or $M_2$) and finish the transformation at a relatively lower so-called "Martensite-Finish temperature" ($M_f$ or $M_1$), below which the material exists as martensite, exhibiting shape recovery. Such phase transformations induced by thermal stimulus is illustrated in FIG. 10. Due to material hysteresis, phase transformation temperatures at which an SMA material may exist at a similar or comparable phase are not equal. For example, $M_s$ and $A_f$ (or $M_f$ and $A_s$) at which a SMA material exists in similar phases are not equal. In general, an "Austenite-Finish temperature ($A_f$) is utilized to characterize the shape memory and hyperelasticity effects of an SMA material.

In addition to thermal stimulus, phase transformation-to-martensite or phase transformation-to-austenite of an SMA material may take place under other stimulus, such as applied force or stress. For example, for an SMA material that exists as austenite at the temperature of interest that is slightly below its active "Austenite-Finish temperature" $A_f$ (or comparably "Martensite-Start temperature" $M_s$), applied stress may "force" the material to undergo the phase transformation-to-martensite, at which the material would exhibit considerable deformation for a relatively small applied force or stress. Once the force or stress is released, the material in martensite reverts back to austenite and recovers its original shape (the memory phase). Such phase transformation-to-martensite effect as induced by external force or stress makes an SMA material appears to be extremely elastic, and is known as superelasticity. This superelasticity is used for the selection of SMA materials for fabricating the cannula strut herein.

Examples of SMA materials include, but are not limited to, nickel-titanium (nitinol), copper-zinc, copper-zinc-aluminum, copper-aluminum-nickel, and gold-cadmium. Desirably, the shape memory alloy is nickel-titanium (nitinol). For a typical SMA material, its active $A_f$ varies based on the exact composition of the material. In some embodiments, cannula strut 203 comprises a shape memory alloy having an active austenite finish temperature ($A_f$) that is near or below the body temperature of the patient. In humans, that temperature is generally about 98.6° F. or 37° C. In some aspects, the $A_f$ of the shape memory alloy is from 0° C. and 35° C. In yet another aspect, the $A_f$ is from 5° C. to 30° C. In yet another aspect, the $A_f$ is from 10° C. to 25° C. In still yet another aspect, the $A_f$ is from 10° C. to 20° C. In some embodiments, cannula strut 203 comprises nitinol.

Self-expanding cannula 300 as described herein further comprises first balloon film 310 and second balloon film 320 as noted above. In some embodiments, one or both of the balloon films comprise a plurality of layers (see FIG. 6, for example). In some embodiments, one or both of the balloon films comprise two layers. In other embodiments, one or both of the balloon films comprise three layers. In still other embodiments, one or both of the balloon films comprise more than three layers. Each layer of first balloon film 310 or second balloon film 320 may be the same or different from any other layer. For first balloon film 310 having a plurality of layers, its surface layer defines interior surface 161 of cannula 300 that is exposed, or adjacent, to the impeller blade, with a minimal clearance. For second balloon film 320 having a plurality of layers, its surface layer defines exterior surface 163 of cannula 300 that is exposed to the surface of the blood vessels and the center lumen of outer sheath assembly 121. Interior surface 161 and exterior surface 163 will be directly exposed to the blood. In all aspects, the circumference of exterior surface 163 is larger than the circumference of the interior surface 161.

The distance between interior surface 161 and exterior surface 163 defines the total thickness of elongate, fluid-impermissible wall structure 159 that comprises cannula 300. In some aspects the thickness of the cannula wall is from 25 µm to 250 µm. In yet another aspect, the thickness of the cannula wall is from 50 µm to 150 µm. In still yet another aspect, the thickness of the cannula wall is about 50 µm, about 75 µm, about 100 µm, about 125 µm, about 150 µm, about 175 µm, about 200 µm, about 225 µm, or about 250 µm.

The thickness of elongate, fluid-impermissible wall structure 159 of cannula 300 is determined by the thickness of first balloon film 310, the thickness of second balloon film 320, and the thickness of cannula strut 203. In some aspects the thickness of first balloon film 310 and second balloon film 320 is each independently from 10 µm to 200 µm thick. In some aspects, the thickness of each film is about 10 µm, about 20 µm, about 30 µm, about 40 µm, about 50 µm, about 60 µm, about 70 µm, about 80 µm, about 90 µm, about 100 µm, about 110 µm, about 120 µm, about 130 µm, about 140 µm, about 150 µm, about 160 µm, about 170 µm, about 180 µm, about 190 µm, or about 200 µm.

Figure 6A:
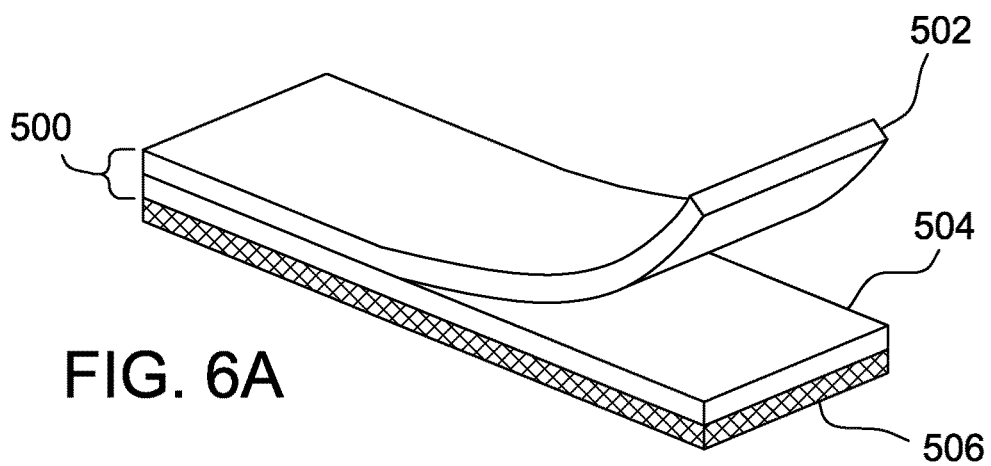
FIGS. 6A, 6B, and 6C illustrate various embodiments of a collapsible and self-expandable cannula including a strut, a first balloon film and a second balloon film where each film comprises various polymer layers.
Figure 6B:
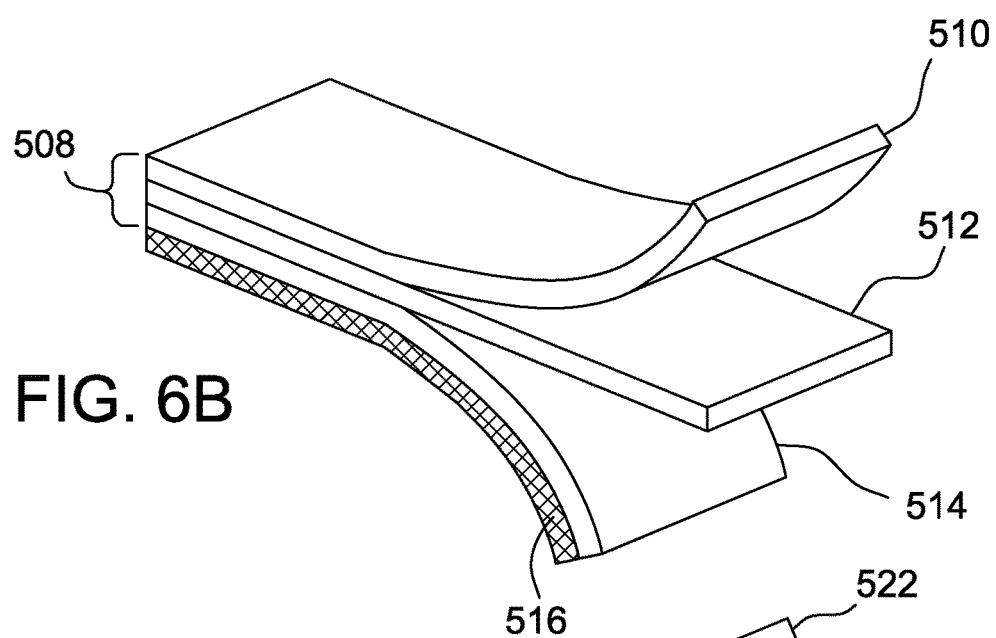
Figure 6C:
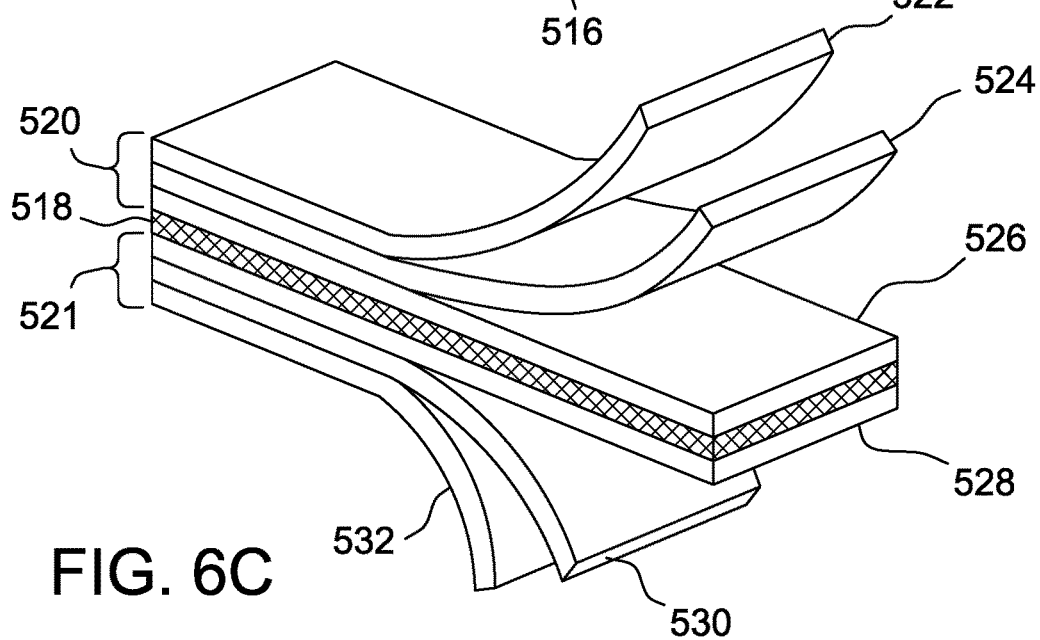

Referring now to FIG. 6A, there is illustrated a balloon film 500 including a first layer 502 and a second layer 504 such that balloon film 500 includes two layers. Second layer 504 is in contact with shape memory alloy 506 (i.e., cannula strut 203) and second layer 504 is also in contact with first layer 502. Referring now to FIG. 6B, there is illustrated a balloon film 508 including a first layer 510, a second layer 512, and a third layer 514 such that balloon film 508 includes three layers. Second layer 512 is sandwiched between first layer 510 and third layer 514 and third layer 514 is in contact with shape memory alloy 516 (i.e., cannula strut 203). Referring now to FIG. 6C, there is illustrated a shape memory alloy 518 (i.e., cannula strut 203) being encapsulated by a first balloon film 520 and a second balloon film 521. First balloon film 520 includes a first layer 522, a second layer 524, and a third layer 526. Second balloon film 521 includes a first layer 528, a second layer 530, and a third layer 532.

As noted above, one or both of first balloon film 310 and second balloon film 320 may include one, two, three or more layers. In many embodiments, one or more layers are desirably biocompatible, and generally include a biocompatible polymer. In some aspects the polymer is a biocompatible thermoplastic elastomer. Each layer of first balloon film 310 and second balloon film 320 may be the same or different. In some embodiments, each biocompatible thermoplastic elastomer is independently selected from the group consisting of a polyurethane block copolymer having both hard blocks and soft blocks, a poly(ether amide) block copolymer, a poly(ether ester) block copolymer, a functionalized polyolefin polymer (olefinic) or copolymer grafted with polar functional groups, a functionalized polystyrene (styrenic) copolymer grafted with polar functional groups and combinations thereof. In some embodiments, the biocompatible thermoplastic elastomer comprises a polyolefin polymer (olefinic) or copolymer grafted with polar functional groups and/or a polystyrene (styrenic) copolymer grafted with polar functional groups where the polar functional groups are selected from the group consisting of maleic anhydride, acrylate, epoxy, amine, and combinations thereof. Desirably, in many embodiments, the biocompatible thermoplastic elastomer for the first balloon film, the second balloon film or both is a thermoplastic polyurethane material.

In another embodiment, the biocompatible thermoplastic elastomer is selected from the group of segmented polyurethane block copolymers that comprises the hard urethane segment/block chemically derived from an aromatic or aliphatic diisocyanate and a diol or diamine chain extender and the soft segment/block chemically derived from one or more polyglycol(s) such as polyester glycol(s), polyether glycol(s), polycarbonate glycol(s), dihydroxylated silicone polymer(s) and any combinations thereof. For example, commercially available Tecoflex™ thermoplastic polyurethane resins comprises a family of aliphatic poly(ether urethane) block copolymers whose hard block is chemically derived from 4,4'-methylenebis(cyclohexyl isocyanate) and 1,4-butane diol, and soft blocks from polyether glycol (poly(tetramethylene oxide) glycol). For another example, commercially available Elast-Eon™ or Pursil® thermoplastic polyurethane resins comprise a family of silicone-poly (ether urethane) copolymers whose hard blocks are chemically derived from an aromatic isocyanate (i.e. methylene diphenyl diisocyanate) and 1,4-butane diol, soft blocks from two different polyglycols, including a dihydroxylated polydimethylsiloxane polymer and a polyether glycol. For yet another example, commercially available Pellethane® or Elasthane™ thermoplastic polyurethane resins comprise a family of poly(ether urethane) copolymers whose hard blocks are chemically derived from an aromatic isocyanate (i.e. methylene diphenyl diisocyanate) and 1,4-butane diol and soft blocks from polyether glycol (i.e. poly(tetramethylene oxide) glycol). For a first or second balloon film, each comprising only one layer, a biocompatible thermoplastic polyurethane resin is preferably used as the balloon material. Such a polymer may be selected from the group comprising poly(ether-urethane) resin family (Elasthane™, Pellethane®, and the like), or silicone-poly(ether-urethane) resin family (Pursil®, Elast-Eon®, and the like), or poly (carbonate-urethane) resin family (Bionate® and the like), or silicone-poly(carbonate-urethane) resin family (Carbosil® and the like), or combinations thereof.

In some embodiments, a polymer blend or admixture comprising two or more thermoplastic polyurethane resin material(s) having different hard-block and/or soft-block types may be used for one or both of first balloon film 310 or second balloon film 320 that comprises only one layer. For example, a poly(ether urethane) block polymer resin can be blended or admixed with a silicone-poly(ether urethane) block copolymer and used as a balloon material for first balloon film 310 and/or second balloon film 320.

In yet another aspect, first balloon film 310 or second balloon film 320 may comprise two or more layers. The top layers of the balloon films may comprise a nonpolar olefinic thermoplastic elastomer having good surface lubricity.

In some aspects where first balloon film 310, second balloon film 320, or both comprise three layers, the intermediate layer (that is, the layer between the inner and outer layers) comprises a polymer that is adhesive and will facilitate attachment of the other two layers. Some adhesive polymers have linking or coupling functional groups including, but not limited to, maleic anhydride, acrylic monomers, epoxy and amine groups.

In still yet another aspect, first balloon film 310 and/or second balloon film 320 may comprise two or more film layers. The top layers of the balloon films may be selected from fluorinated thermoplastic elastomer polymers. Examples of fluorinated elastomer polymers include, but are not limited to, fluorinated ethylene-propylene copolymer, perfluoroalkoxy alkane polymer, and the like. These polymers may be used individually or incorporated as a polymer blend with any other polymer disclosed herein.

c. Manufacturing the Collapsible and Self-Expanding Cannula

Also disclosed herein are methods for manufacturing collapsible and self-expandable cannula 300 as described herein for use with a percutaneous heart pump or other medical device. Fabrication of cannula 300 may be done using a two-step process in many embodiments. In the first step, first balloon film 310 and second balloon film 320 are prepared using a suitable blow molding process. In the second step, the prepared first balloon film 310 and second balloon film 320 are assembled with cannula strut 203 (generally constructed from an SMA) and integrated into a hybrid structure from the inward radial pressure of a shrink tube used in the manufacturing process as described herein.

Figure 9A:
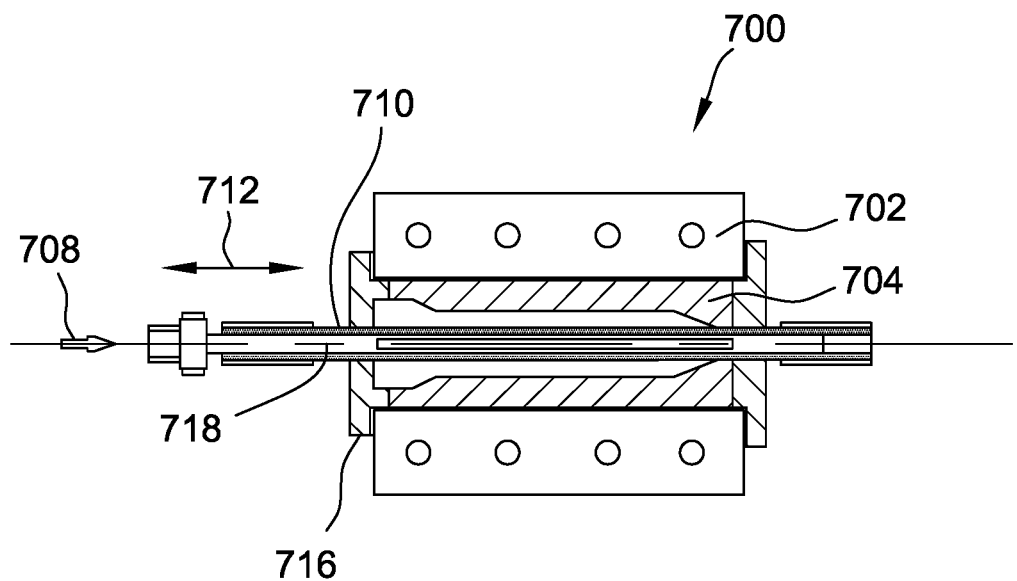
FIGS. 9A and 9B illustrate a blow molding device comprising a thermal module, a blow mold, and a blowing mandrel mounted on a movable cartridge and having a gas inlet. Shown is one embodiment before blowing (FIG. 9A) and after blowing (FIG. 9B).
Figure 9B:
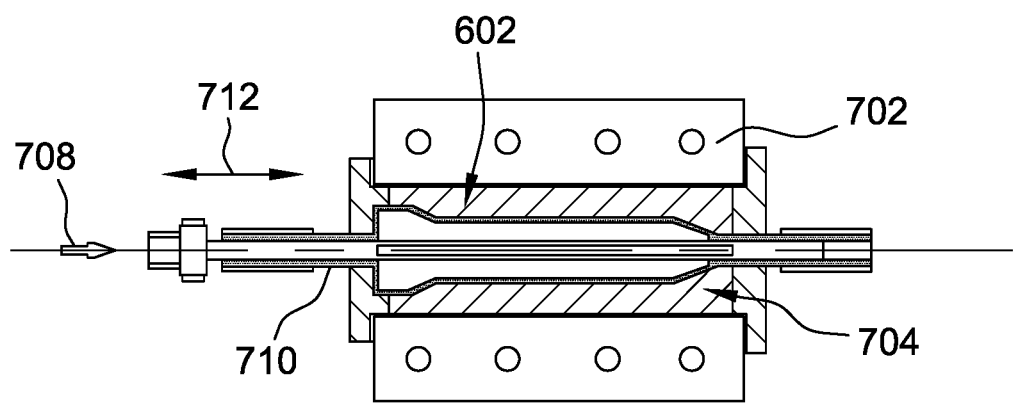

In many embodiments, first balloon film 310 and/or second balloon 320 film are prepared from a polymer parison 710 using a blow molding device 700 (See FIGS. 9A and 9B). Polymer parison 710 comprises an extruded tube from any polymer or a coextruded tube from any combination of polymers as disclosed elsewhere herein. Polymer parison 710 is introduced onto a blowing mandrel 718 and tightly sealed at its ends by the mold's seal plates 716. Blowing mandrel 718 affixed on moving cartridge 712 moves into and resides inside the cavity of blow mold 704. After closing, the mold and the polymer tube are heated inside blow mold 704 by thermal module 702. A pressurized blowing gas 708 is introduced from the mandrel's gas inlet such that heated polymer parison 710 is blown into a balloon film adapted to the cavity of the mold. After the blow mold 704 is cooled by the thermal module, the blown balloon film is released from the mold and the blowing mandrel 718 and trimmed for making cannula 300. Both first balloon film 310 and second balloon can be prepared in this manner in preparation for fabricating self-expandable and collapsible cannula 300 for a percutaneous heart pump. Other suitable balloon film preparation processes are also within the scope of the present disclosure.

Figure 7A:
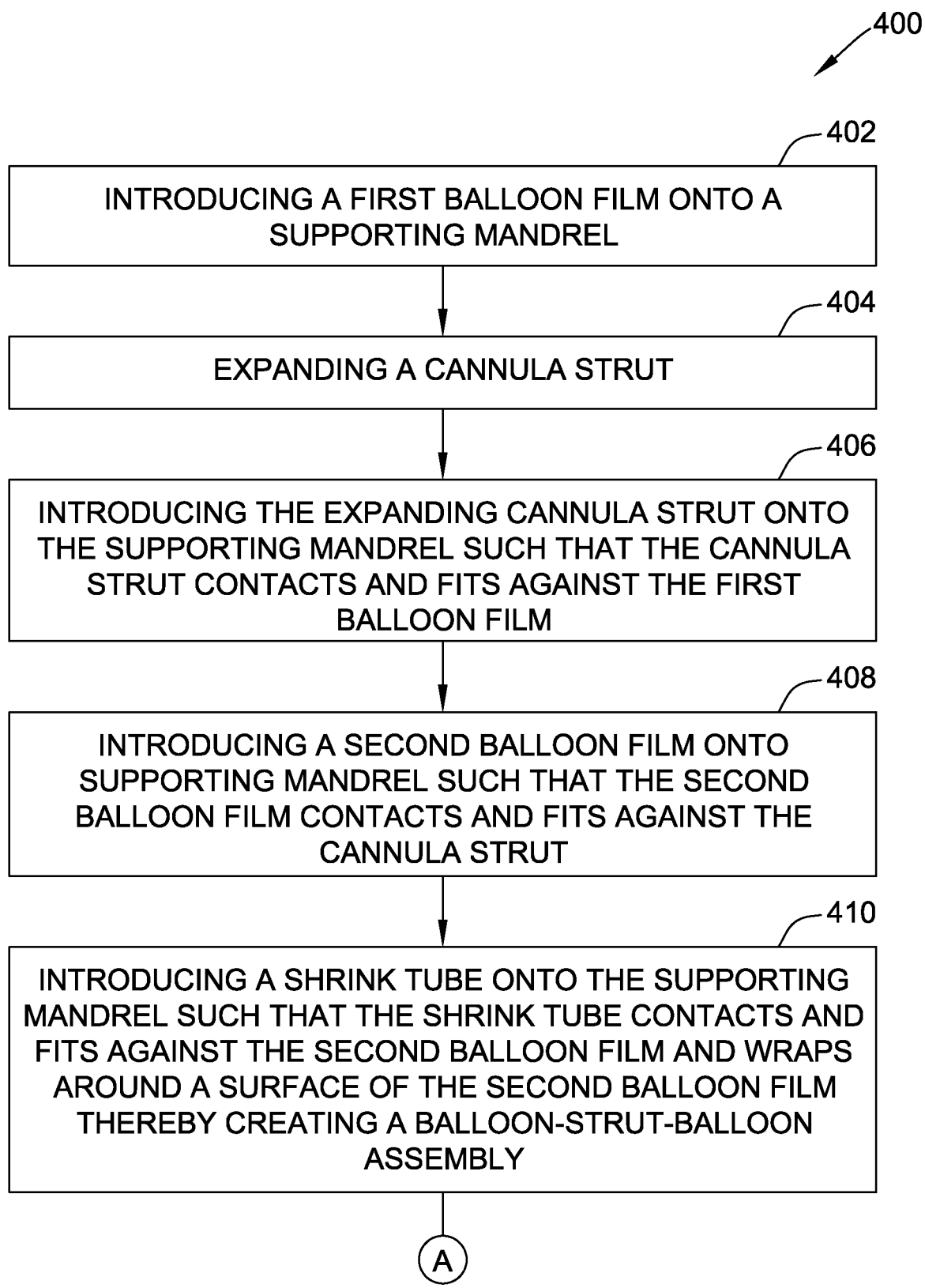
FIGS. 7A and 7B represent a flow diagram illustrating one embodiment of a method to manufacture a collapsible and self-expandable cannula.
Figure 7B:
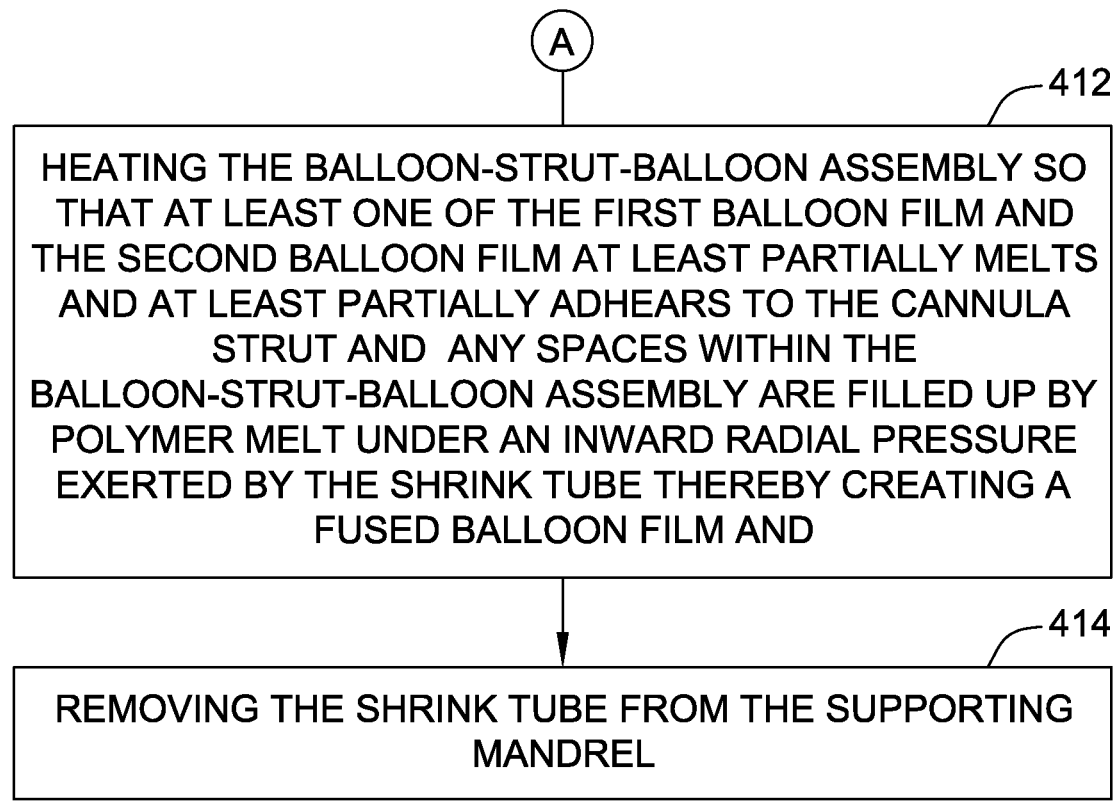

Also disclosed herein is a specific method for forming and manufacturing collapsible and self-expanding cannula 300 that comprises a first balloon film 602 that defines first balloon film 310 (shown in FIG. 5), cannula strut 203, and a second balloon film 604 that defines second balloon film 320 (shown in FIG. 5). FIGS. 7A and 7B are a flow diagram illustrating such a method 400, and FIGS. 8A-8E are schematic diagrams illustrating performance of method 400.

Referring now to FIGS. 7A and 7B, in one embodiment, method 400 comprises introducing 402 first balloon film 602 onto a supporting mandrel 600; expanding 404 cannula strut 203; introducing 406 expanded cannula strut 203 onto supporting mandrel 600 such that cannula strut 203 contacts and fits against first balloon film 602; introducing 408 second balloon film 604 onto supporting mandrel 600 such that second balloon film 604 contacts and fits against cannula strut 203; introducing 410 a shrink tube 606 onto supporting mandrel 600 such that shrink tube 606 contacts and fits against second balloon film 604 and wraps around the outer surface of second balloon film 604 thereby creating a balloon-strut-balloon assembly; heating 412 the balloon-strut-balloon assembly so that at least one of first balloon film 602 and second balloon film 604 at least partially melts and at least partially adheres to cannula strut 203 such that spaces within the balloon-strut-balloon assembly are filled up by polymer melt under an inward radial pressure exerted by shrink tube 606 thereby creating a fused hybrid balloon film; and removing 414 shrink tube 606. It is understood that numerous modifications can be made to this method and that other arrangements can be devised without departing from the spirit and scope thereof. As one non-limiting example, in some embodiments, cooling of the final fused balloon film is done before removing shrink tube 606. In yet another embodiment, cooling of the final fused balloon film is done after removing shrink tube 606.

Figure 8A:
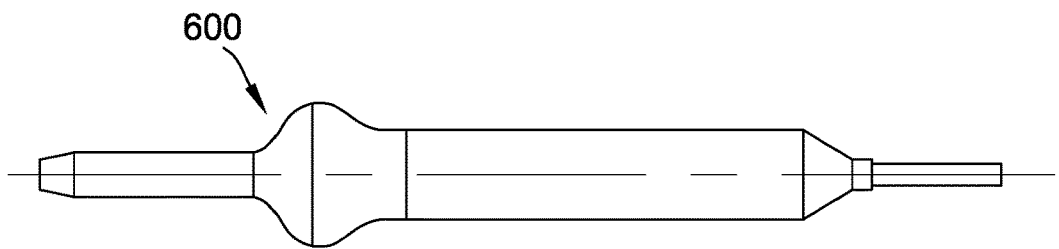
FIGS. 8A, 8B, 8C, 8D and 8E illustrate a supporting mandrel in which a first balloon film, a cannula strut and a second balloon film have been introduced: 8A illustrates the smooth supporting mandrel coated with polytetrafluoroethylene material providing the free release of the polymer material from the coated surface; 8B illustrates the supporting mandrel with the first balloon film introduced; 8C illustrates the supporting mandrel with the first balloon and the cannula strut; 8D illustrates the balloon-strut-balloon assembly comprising a first balloon film, a cannula strut and a second balloon film; and 8E illustrates the balloon-strutballoon assembly encapsulated by a shrink tube and the inward radial pressure exerted thereby on the balloon-strut-balloon assembly.
Figure 8B:
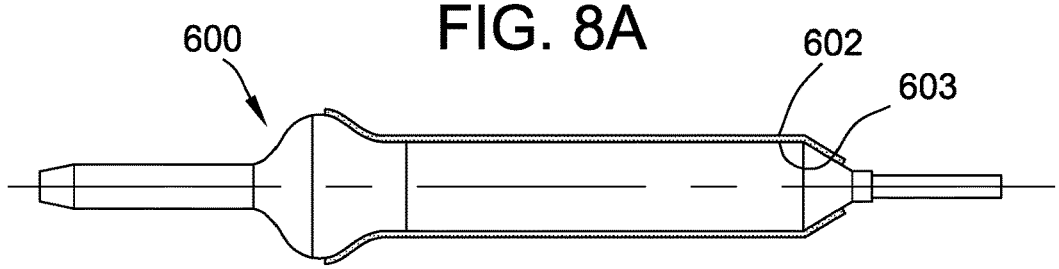
Figure 8C:
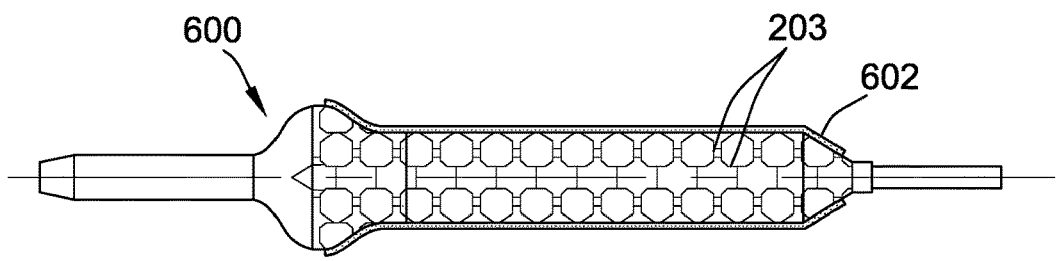
Figure 8D:
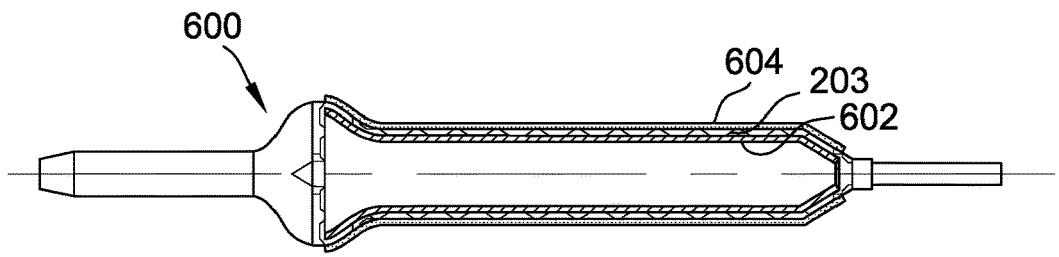
Figure 8E:
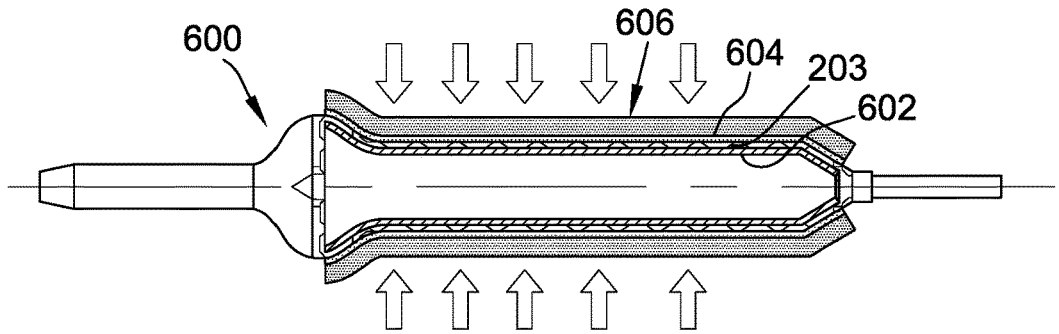

Referring generally now to FIGS. 8A-8E and in further reference to forming and manufacturing collapsible and self-expanding cannula 300 that comprises first balloon film 602 that defines first balloon film 310 (shown in FIG. 5) and second balloon film 604 that defines second balloon film 320, FIG. 8A illustrates empty supporting mandrel 600 for forming collapsible and self-expanding cannula 300 having an elongate fluid-impermissible wall structure 159 extending from open proximal end 183 to open distal end 184 of cannula 300. FIG. 8B shows first balloon film 602 introduced onto the outer profile surface of supporting mandrel 600 after being trimmed, inserted and properly positioned. FIG. 8C shows cannula strut 203 being introduced onto and against first balloon film 602 that is properly situated on supporting mandrel 600. Cannula strut 203 is expanded before being placed onto supporting mandrel 600. FIG. 8D shows second balloon film 604 introduced overtop of cannula strut 203 such that all three components of this embodiment: first balloon film 602, cannula strut 203 and second balloon film 604, are all properly situated on supporting mandrel 600 thereby forming a hybrid balloon-strut-balloon assembly. FIG. 8E shows shrink tube 606 being introduced to fully wrap around and encapsulate the balloon-strut-balloon assembly, including open proximal end 183 and open distal end 184. FIG. 8E further illustrates the application of an inward radial pressure in conjunction with heat on shrink tube 606 to a temperature at which first balloon film 602 and/or second balloon film 604 at least partially melts to fill any gaps or spaces within the balloon-strut-balloon assembly. The pressure of shrink tube 606 in conjunction with heat forces first balloon film 602 and/or second balloon film 604 to encapsulate and adhere to the surface of cannula strut 203.

Heat to the balloon-strut-balloon assembly (including shrink tube 606) can be supplied from any convenient source (not shown in the Figures), including, but not limited to, an oven, a vacuum oven, an induction heater, an RF heater, an IR heater, and the like. When first balloon film 602 and/or second balloon film 604 are heated above their melting or glass transition temperatures, they will at least partially (and in many embodiments, completely) melt and begin to flow. The first balloon film 602 and second balloon film 604, under radial, compressive pressure from shrink tube 606, will flow through the structural spaces of cannula strut 203 such that first balloon film 602 and second balloon film 604 contact one another and at least partially (and in many embodiments, completely) flow together. This creates an integrated structure between first balloon film 602 and second balloon film 604 such that the boundary or surface of each balloon film is not clearly delineated. This integration of first balloon film 602 and second balloon film 604 greatly reduces or even eliminates delamination of elongated, fluid impermissible wall structure 159 of self-expanding cannula 300 during operation of the percutaneous heart pump.

After fusing together as one hybrid entity, the thermally-integrated balloon-strut-balloon assembly may be naturally or forcibly cooled. After the desired cooling, shrink tube 606 is then removed. Even without trimming, the resultant assembly comprises finished cannula 300 having elongated fluid-impermissible wall structure 159 with an internal profile surface conforming to the external profile surface of supporting mandrel 600, open proximal end 183, and open distal end 184 (shown in FIGS. 2 and 3). It is understood that first balloon film 602 and second balloon film 604 may comprise a plurality of layers as discussed herein and previously illustrated in FIGS. 6A, 6B and 6C. All three components in such a hybrid cannula are thermally fused together before the shrink tube 606 is removed. By properly selecting a combination of different polymer materials for each layer of the first balloon film 602 and/or second balloon film 604 as disclosed elsewhere herein, elongate fluid-impermissible wall structure 159 of cannula 300 will exhibit strong adherence from one layer to another and between catheter strut 203 and the layers with which catheter strut 203 is in direct contact. Additionally, such an elongated wall structure 159 has minimal or no impact on the collapsibility and self-expanding of "bare" cannula strut 203. Furthermore, delamination between any balloon film layers and from the metallic surfaces of cannula strut 203 is eliminated.

In some desirable embodiments, the ends of the thermally-integrated first and second balloon films are trimmed such that a fluid-impermissible elongate wall structure 159 comprising the cannula is at least as long as an impeller 165 (see FIG. 3) of the percutaneous heart pump and slightly longer than the maximum thickness of the aortic valve of a typical patient.

In many embodiments of the illustrated method, shrink tube 606 exerts an inward radial pressure on first balloon film 602, cannula strut 203 and second balloon film 604 upon heating the assembly as shown in FIG. 8E. The thickness of the newly formed elongate fluid-impermissible wall can be of any desired thickness, as noted above. Heating the balloon-strut-balloon assembly fuses first balloon film 602 and second balloon film 604 onto cannula strut 203 and onto each other in order to make a fully integrated and continuous surface and fluid-impermissible wall of the self-expanding cannula. In many embodiments, the polymer or polymers selected for each of the layers of first balloon film 602 and second balloon film 604 are desirably selected such that, when melted, they readily fuse and integrate together. The temperature to which the balloon-strut-balloon assembly is heated will vary based on the critical thermal transition temperatures, namely the melting temperatures for semicrystalline polymers or glass transition temperatures for amorphous polymers that comprise first balloon film 602 and second balloon film 604. In some embodiments, the heating is above 50° C., above 75° C., above 100° C., above 125° C., above 150° C., above 175° C. or above 200° C. Desirably, the temperature is between 100° C. and 250° C.

Because shrink tube 606 is removed from the self-expanding cannula after its manufacture, shrink tube 606 is generally formed from a material that is stable to the temperatures achieved in the manufacturing process and does not stick/adhere to the surface (outer) layer of second balloon film 604 to which it contacts to provide the above-described pressure. Desirably, in many embodiments shrink tube 606 is a fluorinated polymer or a fluoropolymer, such as polytetrafluoroethylene, perfluoroalkoxy polymer, fluorinated ethylene-propylene copolymer, ethylene-teterfluoroethylene copolymer or the like that is highly resistant to polymer adhesion.

Although the embodiments and examples disclosed herein have been described with reference to particular embodiments, it is to be understood that these embodiments and examples are merely illustrative of the principles and applications of the present disclosure. It is therefore to be understood that numerous modifications can be made to the illustrative embodiments and examples and that other arrangements can be devised without departing from the spirit and scope of the present disclosure as defined by the claims. Thus, it is intended that the present application cover the modifications and variations of these embodiments and their equivalents.

This written description uses examples to disclose the subject matter herein, including the best mode, and also to enable any person skilled in the art to practice the disclosure, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A collapsible and self-expanding cannula for a percutaneous heart pump, the collapsible and self-expanding cannula comprising:
   an open proximal end;
   an open distal end; and
   an elongate, fluid impermissible wall structure; wherein the elongate, fluid impermissible wall structure comprises: (i) a first balloon film disposed on an interior surface of the wall structure and defining a first wall structure circumferential surface; (ii) a second balloon film disposed on an exterior surface of the wall structure and defining a second wall structure circumferential surface; and (iii) a cannula strut disposed between the first balloon film and the second balloon film, wherein the first balloon film, the second balloon film, and the cannula strut are a fused integrated structure having a substantially smooth, continuous inner surface and a substantially smooth, continuous outer surface, wherein a surface layer of the first balloon film comprises a biocompatible first thermoplastic elastomer, and a surface layer of the second balloon film comprises a biocompatible second thermoplastic elastomer.

2. The collapsible and self-expanding cannula according to claim 1, wherein the cannula strut comprises a shape memory alloy.

3. The collapsible and self-expanding cannula according to claim 2, wherein the shape memory alloy has an austenite finish temperature of from 0 to 45° C.

4. The collapsible and self-expanding cannula according to claim 2, wherein the shape memory alloy is a nickel-titanium alloy.

5. The collapsible and self-expanding cannula according to claim 1, wherein the biocompatible first and second thermoplastic elastomers are each selected from the group consisting of a thermoplastic, segmented polyurethane block copolymer, a poly(ether-b-amide) copolymer, poly(ether ester) block copolymer, a functionalized olefinic thermoplastic elastomer having polar functional groups, a styrenic thermoplastic elastomer functionalized by polar functional groups, and combinations thereof, wherein the polar functional groups are selected from the group consisting of maleic anhydride, acrylate, epoxy, amine, and combinations thereof.

6. The collapsible and self-expanding cannula according to claim 1, wherein the self-expanding cannula has a thickness of from about 25 μm to 250 μm.

7. The collapsible and self-expanding cannula according to claim 1, wherein at least one of the first balloon film and the second balloon film comprises at least two polymeric layers.

8. The collapsible and self-expanding cannula according to claim 1, wherein at least one of the first balloon film and the second balloon film comprises three polymeric layers.

9. The collapsible and self-expanding cannula according to claim 1, wherein the biocompatible first thermoplastic elastomer and the biocompatible second thermoplastic elastomer, are independently selected from the group consisting of a thermoplastic polyurethane block copolymers comprising hard blocks and soft blocks of different types, and
wherein the hard blocks and the soft blocks are selected from the group consisting of poly(ether urethane), poly(carbonate urethane), poly(ester urethane), silicone-poly(ether urethane), silicone-poly(carbonate urethane), and a blend or admixture of a combination thereof.

10. The collapsible and self-expanding cannula according to claim 1, wherein the biocompatible first thermoplastic elastomer and the biocompatible second thermoplastic elastomer, are each independently selected from the group consisting of a poly(ether amide) block copolymer, poly (ether ester) block copolymer, a functionalized olefinic thermoplastic elastomer having polar functional groups, a styrenic thermoplastic elastomer functionalized by polar functional groups and combinations thereof, and
wherein the polar functional groups are selected from the group consisting of maleic anhydride, acrylate, epoxy, amine, and combinations thereof.

11. A method of manufacturing a collapsible and self-expanding cannula for a percutaneous heart pump, the method comprising:
introducing a first balloon film onto a supporting mandrel;
expanding a cannula strut;
introducing the expanded cannula strut onto the supporting mandrel such that the cannula strut contacts and fits against the first balloon film;
introducing a second balloon film onto the supporting mandrel such that the second balloon film contacts and fits against the cannula strut;
introducing a shrink tube onto the supporting mandrel such that the shrink tube contacts and fits against the second balloon film and wraps around a surface of the second balloon film thereby creating a balloon-strut-balloon assembly;
heating the balloon-strut-balloon assembly so that at least one of the first balloon film and the second balloon film at least partially melts and at least partially adheres to the cannula strut such that spaces within the balloon-strut-balloon assembly are filled up by polymer melt under an inward radial pressure exerted by the shrink tube thereby creating a fused balloon film; and
removing the shrink tube.

12. The method according to claim 11, further comprising trimming at least one end of the fused balloon film such that the trimmed film forms an elongate fluid-impermissible wall of the self-expanding cannula.

13. The method according to claim 11, wherein at least one of the first balloon film and the second balloon film comprises at least two polymer layers.

14. The method according to claim 11, wherein the first balloon film, the second balloon film, and the cannula strut are fused into an integrated structure having a substantially smooth, continuous inner surface and a substantially smooth, continuous outer surface.

15. The method according to claim 14, wherein the first balloon film and the second balloon film independently comprise a biocompatible thermoplastic elastomer selected from the group consisting of a thermoplastic polyurethane block copolymers comprising hard blocks and soft blocks of different types, and
wherein the hard blocks and the soft blocks are selected from the group consisting of poly(ether urethane), poly(carbonate urethane), poly(ester urethane), silicone-poly(ether urethane), silicone-poly(carbonate urethane), and a blend or admixture of a combination thereof.

16. The method according to claim 14, wherein the first balloon film and the second balloon film independently comprise a biocompatible thermoplastic elastomer selected from the group consisting of a poly(ether amide) block copolymer, poly(ether ester) block copolymer, a functionalized olefinic thermoplastic elastomer having polar functional groups, a styrenic thermoplastic elastomer functionalized by polar functional groups and combinations thereof,
wherein the polar functional groups are selected from the group consisting of maleic anhydride, acrylate, epoxy, amine, and combinations thereof.

17. The method according to claim 11, further comprising cooling the fused balloon film on the supporting mandrel before removing the shrink tube.

\* \* \* \* \*